US00PP26710P3

(12) United States Plant Patent
Pierron-Darbonne

(10) Patent No.: US PP26,710 P3
(45) Date of Patent: May 10, 2016

(54) STRAWBERRY PLANT NAMED 'SAFARI'

(50) Latin Name: ***Fragaria×ananassa* Duchesne ex Rozier**
Varietal Denomination: Safari

(71) Applicant: Plantas de Navarra S.A., Navarra (ES)

(72) Inventor: Alexandre Pierron-Darbonne, Pamplona (ES)

(73) Assignee: PLANTAS DE NAVARRA, S.A. (ES)

( * ) Notice: Subject to any disclaimer, the term of this patent is extended or adjusted under 35 U.S.C. 154(b) by 22 days.

(21) Appl. No.: 14/120,390

(22) Filed: May 16, 2014

(65) Prior Publication Data

US 2014/0352011 P1 Nov. 27, 2014

(30) Foreign Application Priority Data

May 22, 2013 (QZ) ..... PBR 2013/1375

(51) Int. Cl.
*A01H 5/08* (2006.01)

(52) U.S. Cl.
USPC ..... Plt./208
CPC ..... *A01H 5/0893* (2013.01)

(58) Field of Classification Search
USPC ..... Plt./208, 209
CPC ..... A01H 5/0893; A01H 5/08
See application file for complete search history.

*Primary Examiner* — Kent L Bell

(74) *Attorney, Agent, or Firm* — Knobbe, Martens, Olson & Bear, LLP

(57) ABSTRACT

A new and distinct strawberry variety, *Fragaria×ananassa* Duchesne ex Rozier, cv. 'Safari' is characterized by a position of the inflorescence that appears level with the foliage, larger size of calyx relative to corolla, and abundant production of orange red colored, conical shaped, and medium firm fruit, which appears to be characterized by medium fruit size, and early time of flowering and ripening.

13 Drawing Sheets

Latin name of the genus and species claimed: *Fragaria× ananassa* Duchesne ex Rozier.

Variety denomination: 'Safari'.

BACKGROUND AND SUMMARY

The present invention relates to a new and distinct strawberry variety. The varietal denomination of the new variety is 'Safari'. The new variety was designated by the breeder as "06.44H.216". The new variety of strawberry was created by Alexandre Pierron-Darbonne in a breeding program by crossing two parents in 2006 in Cartaya (Huelva), Spain about 7° W., 37° N., 45 feet elevation; in particular, by crossing as seed parent a parent designated "98-126" (unpatented) and as pollen parent a strawberry parent designated "02-105" (unpatented). Seed parent is a selection from breeder's program and has not been commercialized.

The resulting seedling of the new variety was grown and asexually propagated by Alexandre Pierron-Darbonne by runners in 2007 in Segovia, Spain, 3° 59'W., 41° 22'N., 2742 feet elevation and it was successively propagated by runners. Plants of the new variety were further asexually propagated and extensively tested. This propagation and testing has demonstrated that the combination of traits disclosed herein which characterize the new variety are fixed and retained true to type through successive generations of asexual reproduction.

The growing period in Cartaya (Huelva), Spain about 7° W., 37° N., 45 feet elevation is about November 5 until May 15 of each year, with a date of first flowering of November 11. The location where the observations were made is Cartaya (Huelva), Spain and it is believed to apply to plants grown under similar conditions of soil and climate elsewhere.

Among the characteristics which appear to distinguish the new variety from other varieties are a combination of traits which include: inflorescence that appears level with the foliage, large size of calyx relative to corolla, abundant production of orange red colored, conical shaped, and medium firm fruit, medium fruit size, and early time of flowering and ripening.

The new variety 'Safari' is distinguished there from its Seed parent "98-126" (unpatented) in that the seed parent the inflorescence appears under the foliage, it shows a globose shape fruit with an absent or very narrow band without achenes, the seed parent shows a red fruit with a large hollow center and it presents a medium time of flowering and ripening.

The new variety 'Safari' is distinguished there from its pollen parent "02-105" (unpatented) in that the pollen parent the shape base of the terminal leaflet is obtuse and the fruit shows an irregular conical shape with medium glossiness.

The new variety 'Safari' is distinguished from other cultivars by showing the inflorescene at the same level, the shape of base of terminal leaflet is acute, it shows a regular conical shape fruit, it has weak glossiness fruit with a narrow band without achenes, the fruit is orange red with a small hole in the center and it has early flowering and ripening times.

The new variety 'Safari' is closest to the variety 'Sabrina' (U.S. Plant Pat. No. 22,506) but is distinguished the following characteristics possessed by 'Safari' which are different, or not possessed, by 'Sabrina' (U.S. Plant Pat. No. 22,506). The plant habit of 'Sabrina' is upright, whereas 'Safari' is semi-upright (as shown on FIG. 2 and FIG. 3). 'Sabrina' (U.S. Plant Pat. No. 22,506) is more vigorous and dense than 'Safari'. The terminal leaflet of 'Sabrina' is longer than broad, whereas in 'Safari' is as long as broad (as shown on FIG. 7). The leaf of 'Sabrina' shows a stipule with anthocyanin coloration absent or very weak (about Light Green 138D to Light Green 139D), whereas the new variety 'Safari' is weak (about Light Greyed-Red 179D to Medium Greyed-Red 179C) (as shown on FIG. 7 and FIG. 8). The fruit size of 'Sabrina' is larger than the fruit in 'Safari' (as shown on FIG. 12). The fruit color of 'Sabrina' (U.S. Plant Pat. No. 22,506) is red (about Medium Red 43B to Medium Red 43A) with higher firmness, whereas 'Safari' has an orange red fruit color (about Dark Orange-Red 33A to Dark Orange-Red 34A), lightening towards the center (as shown on FIG. 12). The fruits of 'Safari' show a hollow center weakly expressed, whereas the fruits in 'Sabrina' (U.S. Plant Pat. No. 22,506) the hollow center is absent or very weakly expressed (as shown on FIG. 13). The time of beginning of flowering and time of beginning of fruit ripening of 'Safari' is earlier than the time for 'Sabrina' (U.S. Plant Pat. No. 22,506).

BRIEF DESCRIPTION OF PHOTOGRAPHS

The accompanying photographs show typical specimens of the new variety, designated 06.44H.216 in the illustrations, including fruit, foliage and flower, in color as nearly true as it is reasonably possible to make in color illustrations of this character.

The plants depicted in the photographs were planted Oct. 10, 2012 in the in Cartaya (Huelva), Spain, about 7° W., 37° N., 45 feet elevation.

Photographs were taken March-April 2013 (about Mar. 25 and Apr. 8, 2013): minimum temperate about 10 to 12° Centigrade, maximum temperate about 24 to 26° Centigrade.

FIG. 1 shows several plants of the new variety (designated 06.44H.216) which exhibit a semi upright habit, a density plant open and the position of the inflorescence relative to foliage is level with.

Figure 1:
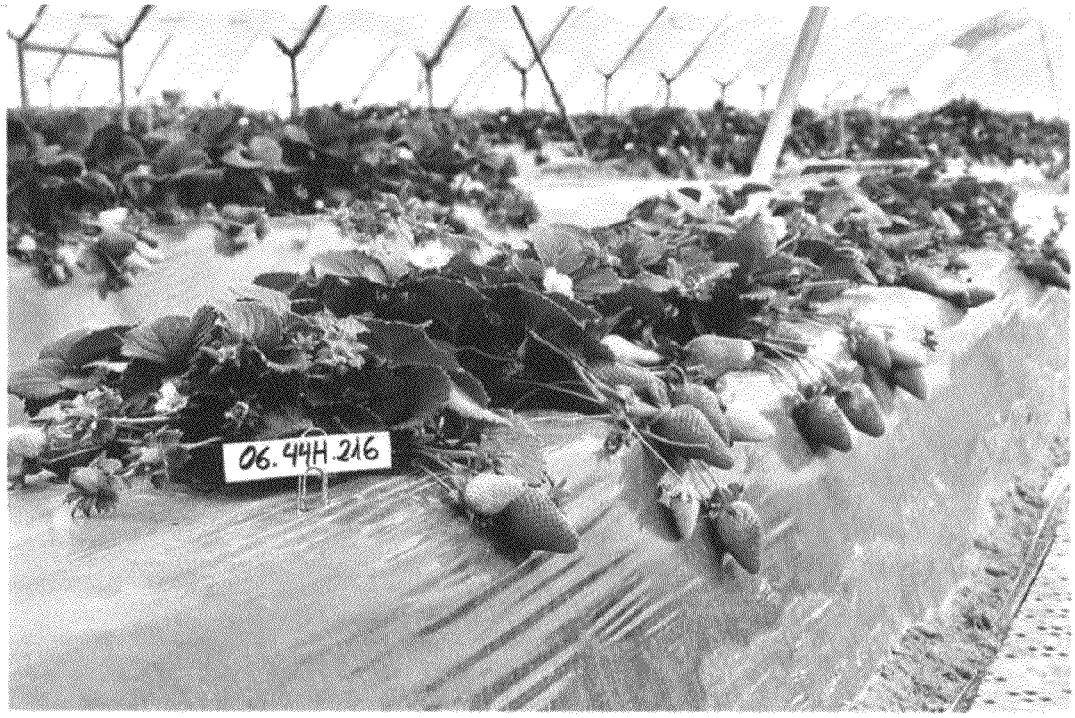
Figure 2:
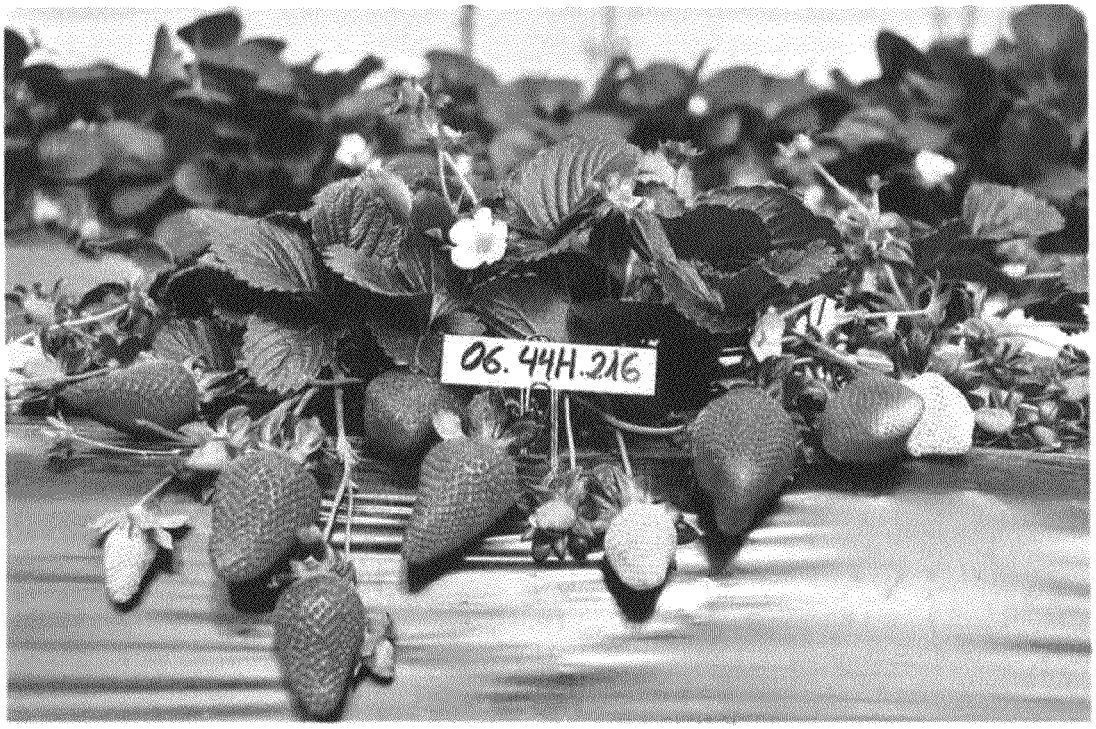
FIG. 2 shows several plants of the new variety (designated 06.44H.216) with several orange red colored and conical shape fruits.
Figure 3:
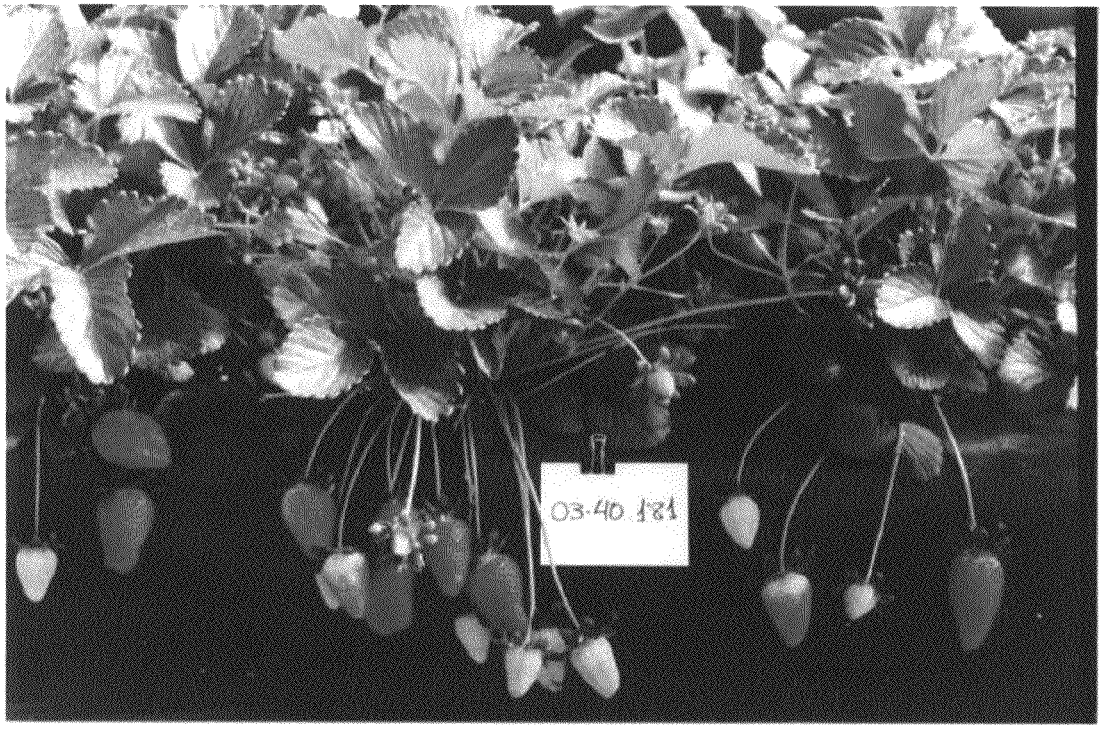

FIG. 3 shows several plants of 'Sabrina' (U.S. Plant Pat. No. 22,506) (designated 03.40.181) with several red colored and conical shape fruits.

Figure 4:
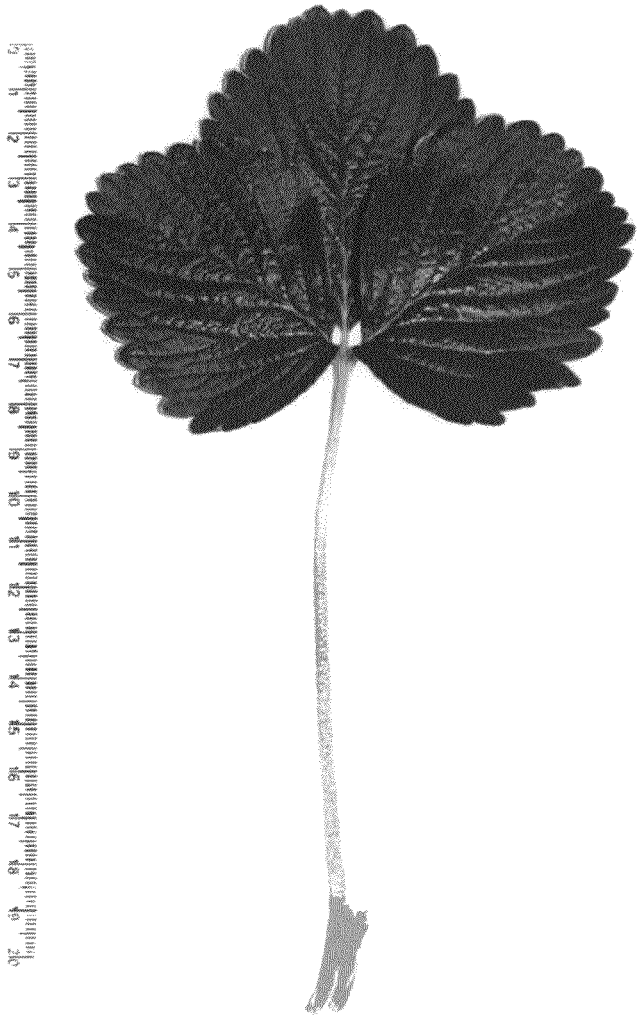

FIG. 4 shows the upper side of a complete leaf of the new variety (designated 06.44H.216). In its we can see that the leaf color of upper side is RHS green group color (about Dark Green 141B to Dark Green 141A) and the stipule shows a weak anthocyanin coloration (RHS about Light Greyed-Red 179D to Medium Greyed-Red 179C).

Figure 5:
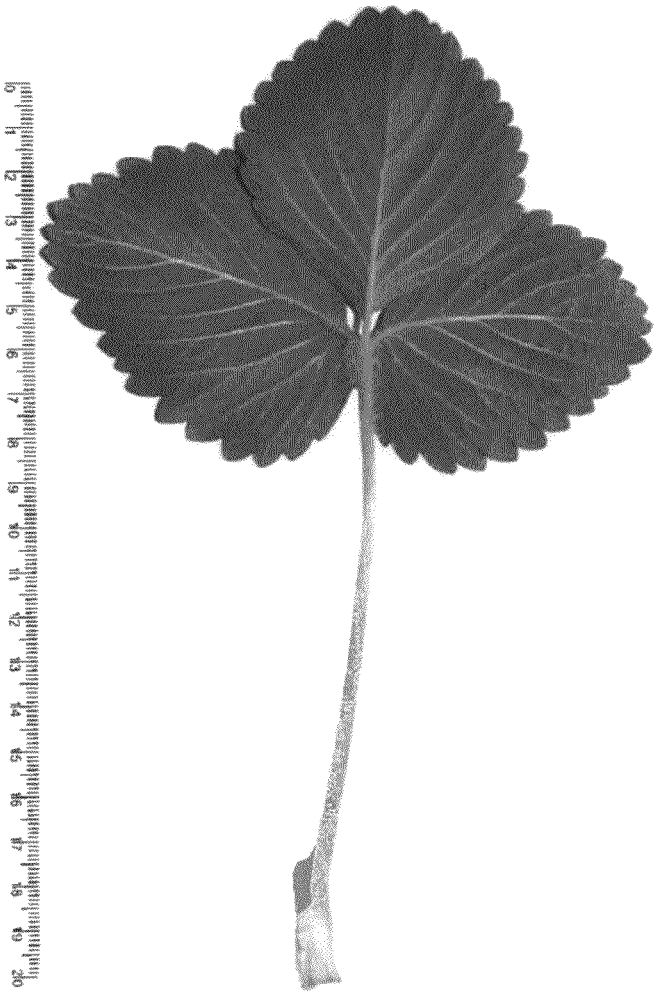

FIG. 5 shows the underside of a complete leave of the new variety (designated 06.44H.216). The leaf color of underside is RHS yellow-green group color (about Medium Green 146D to Medium Green 146B).

Figure 6:
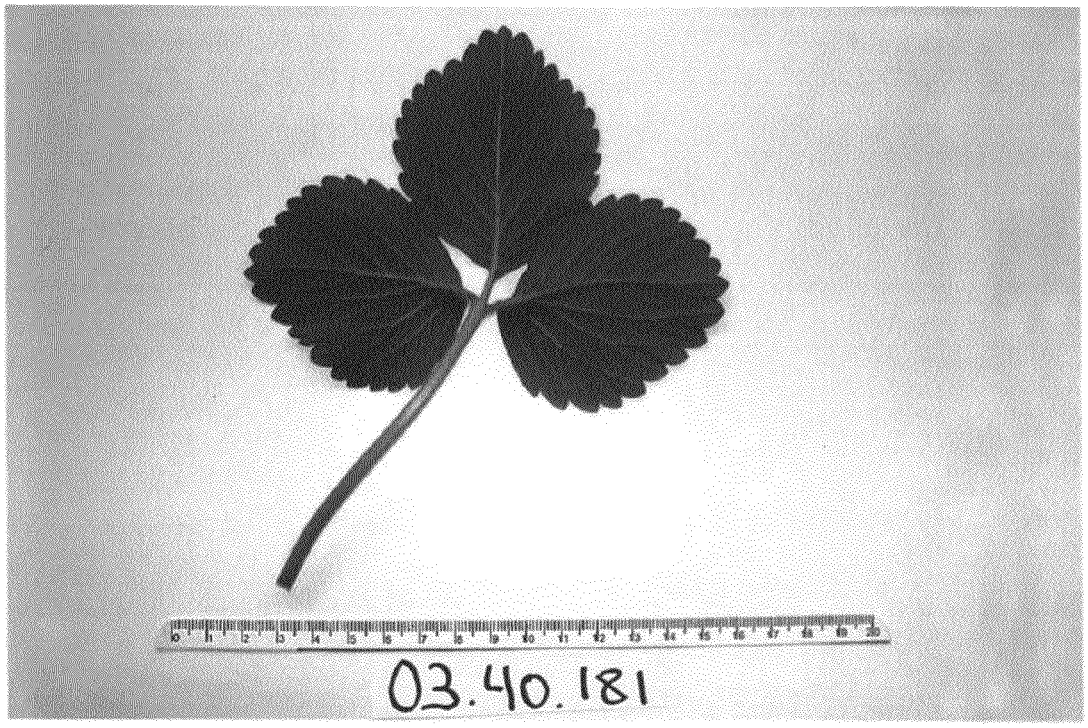

FIG. 6 shows the underside of a complete leave of 'Sabrina' (U.S. Plant Pat. No. 22,506) (designated 03.40.181). In it we can see that the leaf color of underside is RHS green group color (about Medium Green 138B to Medium Green138A).

Figure 7:
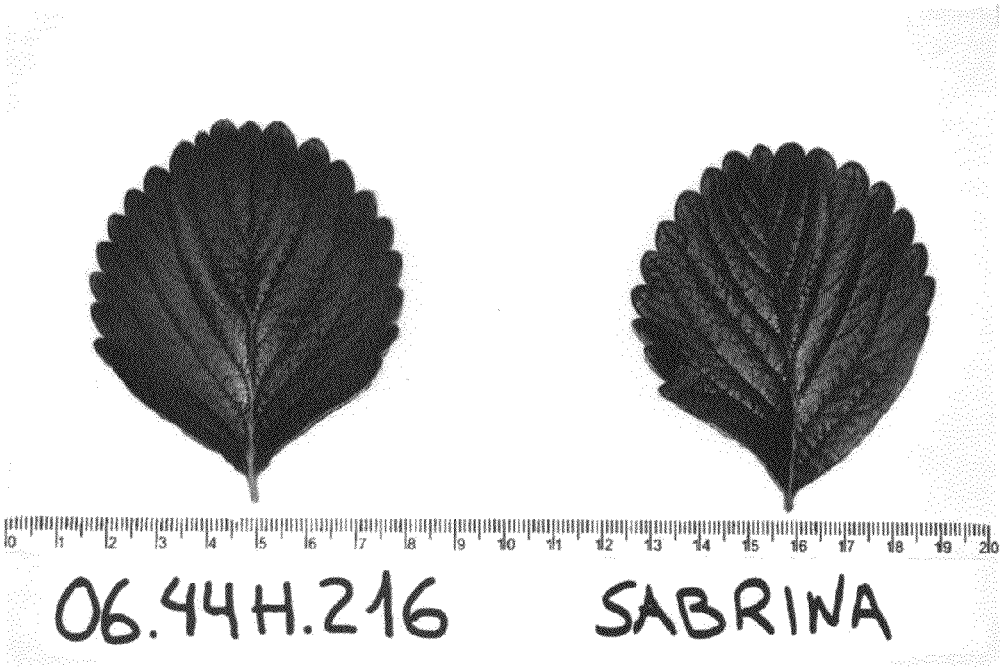

FIG. 7 shows the terminal leaflet of strawberry variety 'Sabrina' (U.S. Plant Pat. No. 22,506) in comparison with the terminal leaflet of the new variety (designated 06.44H.216). We can appreciate that the terminal leaflet in strawberry variety 'Sabrina' (U.S. Plant Pat. No. 22,506) is longer than broad, than in the new variety (designated 06.44H.216) the terminal leaflet is as long as broad.

Figure 8:
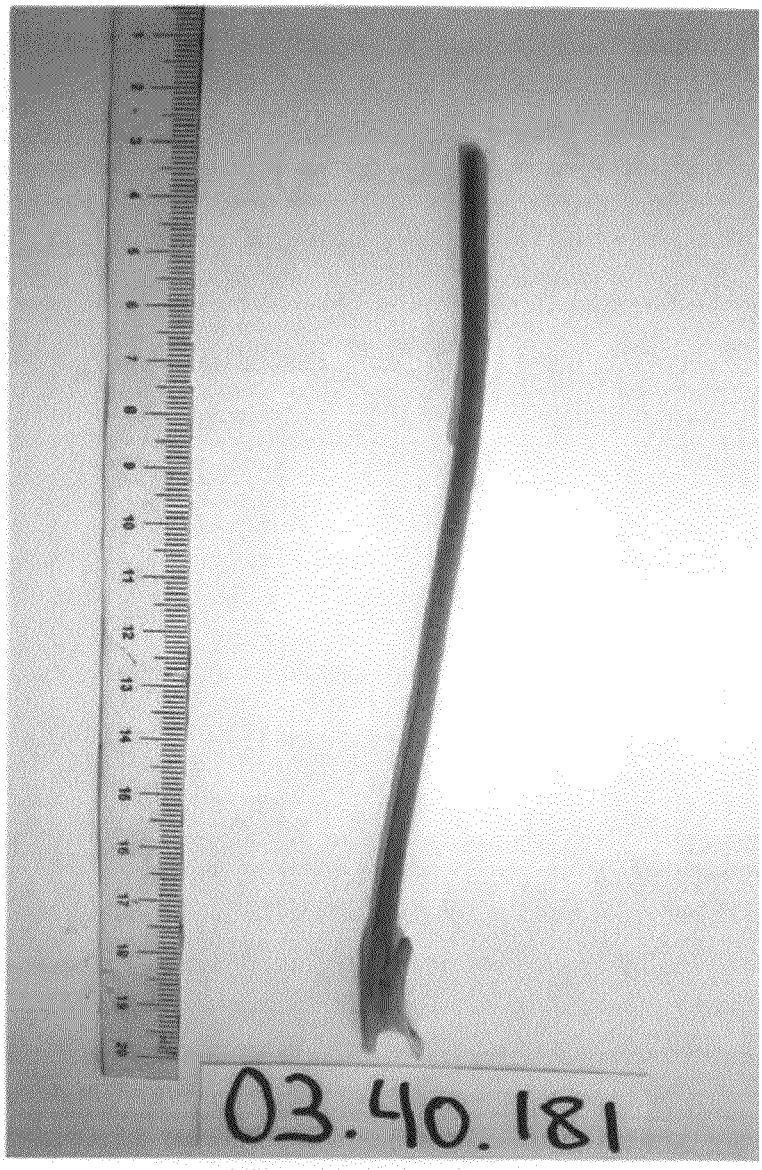

FIG. 8 shows the stipule of 'Sabrina' (U.S. Plant Pat. No. 22,506) (designated 03.40.181) with an anthocyanin coloration absent or very weak (RHS green group about Light Green 138D to Light Green 139D).

Figure 9:
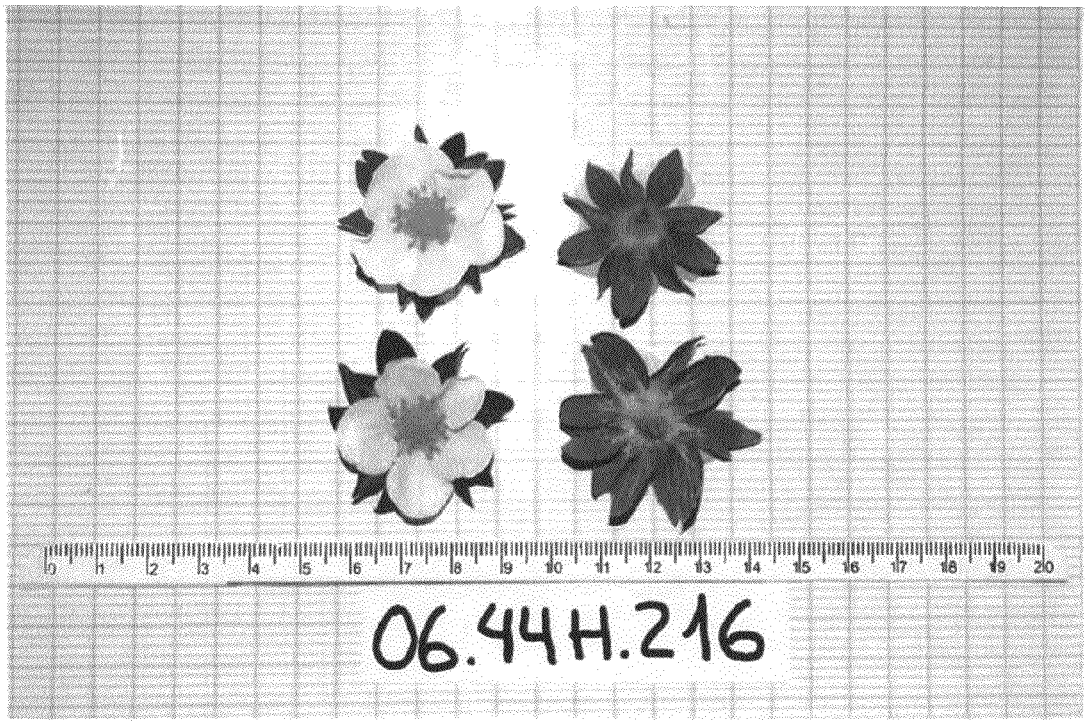

FIG. 9 shows several flowers of the new variety (designated 06.44H.216).

Figure 10:
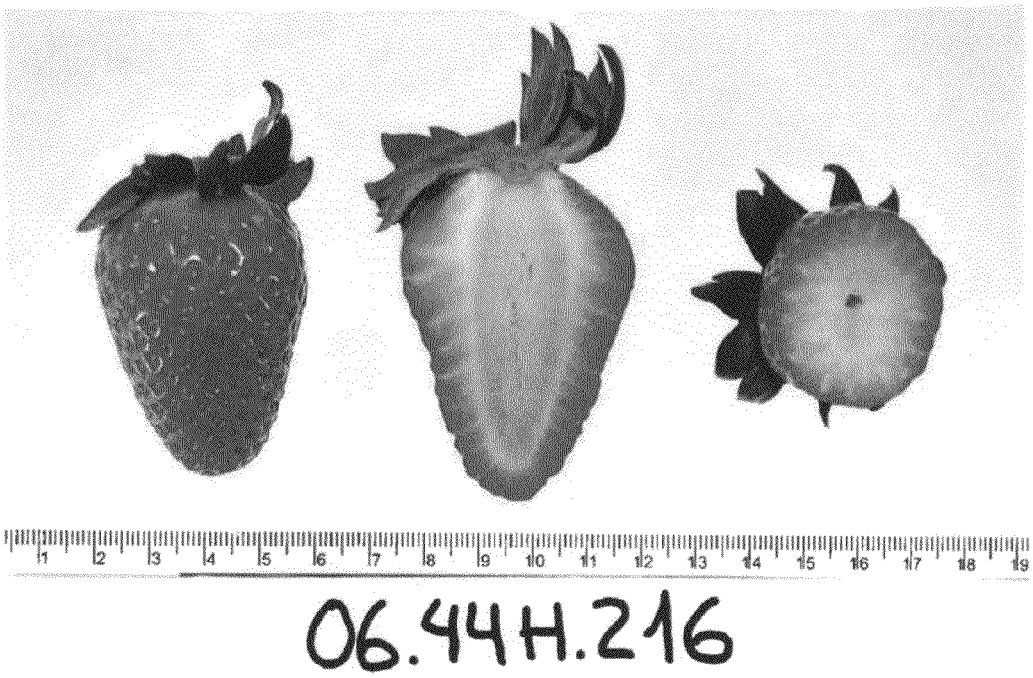

FIG. 10 shows typical fruit of the new variety (designated 06.44H.216) whole, sliced and in cross section, illustrating the typical flesh coloration (RHS orange-red group about Medium Orange-Red 31 C to Dark Orange-Red 33B), lightening toward the center, with a weakly expressed hollow center.

Figure 11:
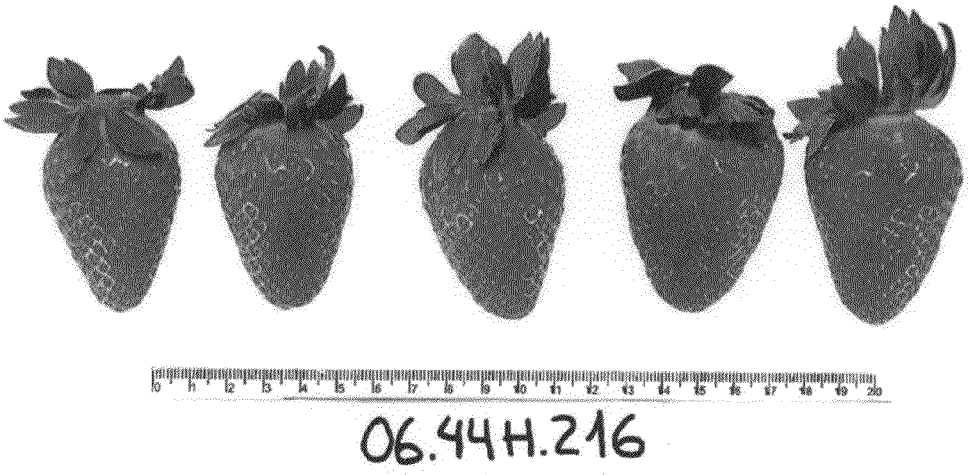

FIG. 11 shows several typical fruits of the new variety (designated 06.44H.216) illustrating the typical conical shape and orange red fruit coloration (RHS orange-red group about Dark Orange-Red 33A to Dark Orange-Red 34A).

Figure 12:
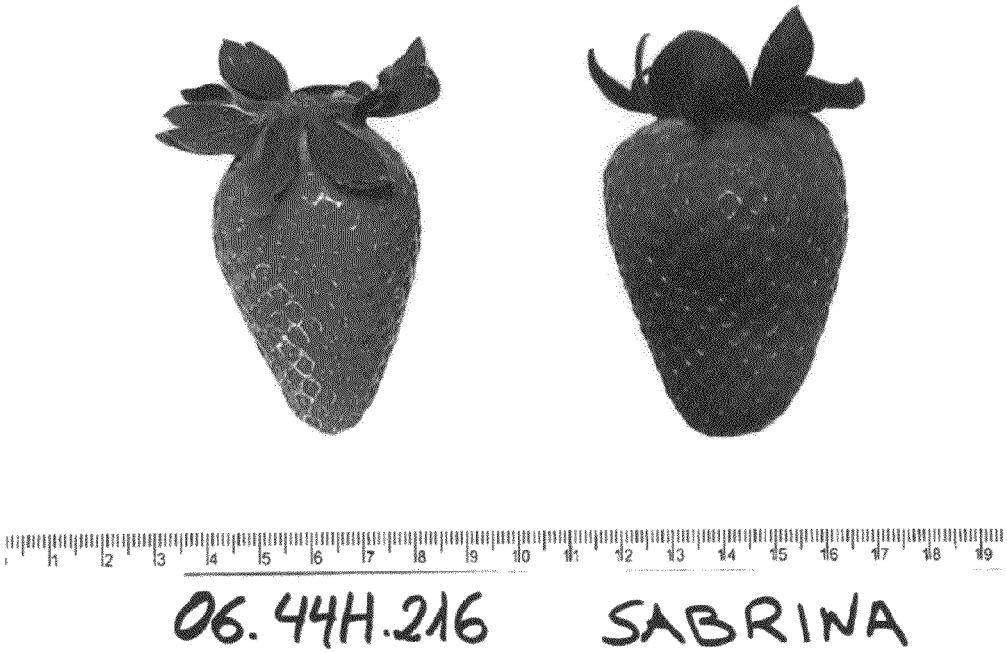

FIG. 12 shows the comparison between whole fruits of the new variety (designated 06.44H.216) and the strawberry variety 'Sabrina' (U.S. Plant Pat. No. 22,506). In it we can see that the fruit size in 'Sabrina' (U.S. Plant Pat. No. 22,506) is larger than in the new variety (designated 06.44H.216) and the fruits of the strawberry variety 'Sabrina' (U.S. Plant Pat. No. 22,506) show a red fruit color (RHS red group about Medium Red 43B to Medium Red 43A), whereas in the new variety (designated 06.44H.216) the fruits show an orange red fruit color (RHS orange-red group about Dark Orange-Red 33A to Dark Orange-Red 34A).

Figure 13:
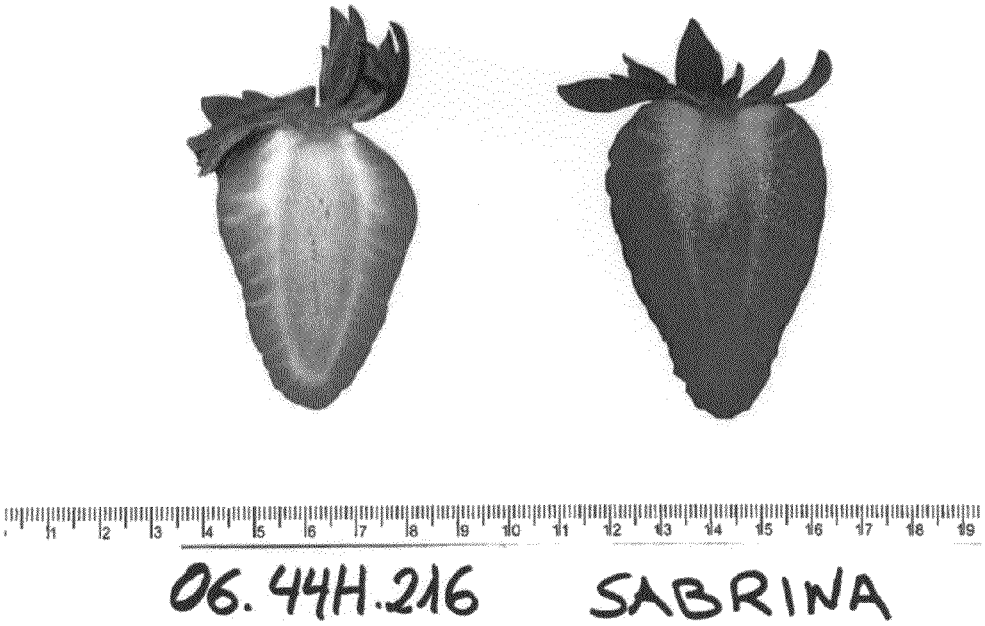

FIG. 13 shows the comparison between sliced fruits of the new variety (designated 06.44H.216) and the strawberry variety 'Sabrina' (U.S. Plant Pat. No. 22,506). In it we can see that the fruit color of flesh in fruits of the strawberry variety 'Sabrina' (U.S. Plant Pat. No. 22,506) is red (RHS red group about Medium Red 41B to Medium Red 41A) and the hollow center is absent or very weakly expressed, whereas the color of flesh in fruits of the new variety (designated 06.44H.216) is orange red (RHS orange-red group about Medium Orange-Red 31C to Dark Orange-Red 33B) and the hollow center is weakly expressed.

DESCRIPTION OF THE NEW VARIETY

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1995. The color descriptions and other phenotypical descriptions may deviate from the stated values and descriptions depending upon variation in environmental, seasonal, climatic and cultural conditions.

The following detailed description of the new variety is based upon observations taken of plants and fruits grown under tunnel, in Cartaya (Huelva), Spain, about 7° W., 37° N., 45 feet elevation on October 10 with a sample size of two repetitions and 225 plants per repetition. After planting, plants are grown in raised beds cover with plastic and with small holes in plastic walls, under tunnels. Water and fertilizer are applied through drip irrigation.

The new variety is principally propagated by way of runners. Although propagation by runners is presently preferred, other known methods of propagating strawberry plants may be used. Strawberries root well after transplanting.

The term "blistering" used herein refers to the texture or rugosity or surface ondulation inherent to leaves and is generally a constant characteristic.

'Safari' is a short day variety that needs an induction to flowering by chilling, such as occurs at high elevation nursery (fresh plant) or with cold storage (referred to as frigo plant). Usually a short time is sufficient. 'Safari' is self-fertile. It produces large quantities of pollen throughout the seasons and pollination is generally good as there are very few malformed fruit.

TABLE 1

Table 1 shows the Accumulated Production of Commercial Quality Fruit (g/plant) of the new variety 'Safari' when compared to its closest varieties 'Sabrina', 'Sabrosa' and 'Camarosa' during the months of February, March, April and May.

| Variety | 21-Fb | 28-Mr | 25-Ap | 15-My |
|---|---|---|---|---|
| SAFARI | 184 | 369 | 605 | 727 |
| SABRINA | 57 | 222 | 762 | 952 |
| SABROSA | 30 | 137 | 530 | 726 |
| CAMAROSA | 34 | 132 | 500 | 662 |

TABLE 2

Table 2 shows the Total Yield to October 17 and fruit weight average of the new variety 'Safari' when compared to its closest varieties 'Sabrina', 'Sabrosa' and 'Camarosa' to May 15.

| Variety | 1st + 2nd Quality Fruit | Total | Weight (g/fruit) |
|---|---|---|---|
| SAFARI | 727 + 202 | 929 | 22-21 |
| SABRINA | 952 + 180 | 1132 | 26-24 |
| SABROSA | 726 + 108 | 834 | 23-22 |
| CAMAROSA | 662 + 320 | 982 | 25-23 |

TABLE 3

Table 3 shows the Production Total, to May 15, of First Quality Fruit ($1^{st}$ quality) and Second Quality Fruit ($2^{nd}$ quality) in g/plant, of the new variety 'Safari' when compared to its closest varieties 'Sabrina', 'Sabrosa' and 'Camarosa.'

| Variety | $1^{st}$ quality | $2^{nd}$ quality | TOTAL ($1^{st}$ quality + $2^{nd}$ quality) | % $2^{nd}$ quality |
|---|---|---|---|---|
| SAFARI | 727 | 202 | 929 | 22 |
| SABRINA | 952 | 180 | 1132 | 16 |
| SABROSA | 726 | 108 | 834 | 13 |
| CAMAROSA | 662 | 320 | 982 | 33 |

$$\%2^{nd}\text{ quality} = \frac{2^{nd}\text{ quality}}{\text{TOTAL}} \times 100$$

TABLE 4

Table 4 shows the Weight (g/Fruit) at two dates: March 28 and May 15 of the new variety 'Safari' when compared to its closest varieties 'Sabrina', 'Sabrosa' and 'Camarosa.'

| WEIGHT (g/fruit) | 28 March | 15 May |
|---|---|---|
| SAFARI | 22 | 21 |
| SABRINA | 26 | 24 |
| SABROSA | 23 | 22 |
| CAMAROSA | 25 | 23 |

WEIGHT is shown as the average weight per fruit in First Quality Fruits.

TABLE 5

Table 4 shows a comparison of the fruit analysis between the new variety 'Safari' and its closest varieties 'Sabrina' and 'Camarosa.'

| FRUIT ANALYSIS | SABRINA | SAFARI (06.44 H.216) | CAMAROSA |
|---|---|---|---|
| Firmness (Kg) | 1.20 | 1.10 | 1.00 |
| Humidity & Volatile Matter (%) | 91.10 | 90.30 | 90.40 |
| Dry Matter (%) | 8.90 | 9.70 | 9.60 |
| PH (to20°) | 3.70 | 3.70 | 3.70 |
| Acidity as Anhydride Citric (%) | 0.60 | 0.50 | 0.60 |
| Soluble Solids (° Brix) | 7.80 | 8.30 | 7.50 |
| Maturity Index | 13.00 | 16.60 | 12.50 |
| Content in Ascorbic Acid (mg/Kg) | 326.7 | 372.00 | 398.30 |
| Dominant Tonality(nm) | 490 | 490 | 495 |
| Luminosity: Transmitance to 460 nm | 30.90 | 35.20 | 31.50 |

The following definitions apply:

Firmness: It is the fruit's resistance to penetration measured in Kilograms (Kg). The measure given has been obtained by the penetrometer ROZE Mod. Arbelette, with a 50 $mm^2$ section head.

Dry Matter: It is the weight of the residual left from the trituration of the fruit after the drying process at a temperature of 103° C.±2° C. until reaching constant weight.

$$(\%)\ \text{Dry Matter} = \frac{\textit{Weigth}\ \text{Dry Matter}}{\textit{Weigth}\ \text{Fresh Matter}} \times 100$$

Humidity & Volatile Matter: Represents the content in volatile matters and water of the fruits.

$$(\%)\ \text{Humidity \& Volatile Matter} = 100 - \%\ \text{Dry Matter}$$

Maturity Index: Relation between Soluble solids and Acidity as Anhydride Citric.

$$\text{Maturity Index} = \frac{\text{Soluble solids}}{\text{Acidity as Anhydride Citric}}$$

DETAILED DESCRIPTION OF THE NEW VARIETY

Plant:
- *Density.*—Sparse.
- *Vigor.*—Medium.
- *Height.*—Medium (About 20 cm).
- *Width.*—Medium (About 21 cm).
- *Growth habit.*—Semi-upright.
- *Position of inflorescence in relation to foliage.*—Same level.
- *Number of stolons.*—Medium.

Stolons:
- *Anthocyanin coloration.*—Medium.
- *Density of pubescence.*—Medium.

Leaf:
- *Size.*—Medium.
- *Upperside.*—RHS green group color (near 141B to 144A).
- *Underside.*—About Medium Green 146D to Medium Green146B).
- *Length.*—Medium, about 8 cm.
- *Width.*—Medium, about 12 cm.
- *Cross section.*—Convex.
- *Leaf surface ondulation or blistering.*—Absent or weak.
- *Number of leaflets.*—Three only.
- *Glossiness.*—Medium.
- *Variegation.*—Absent.
- *Number of leaflets.*—Three only.

Leaf stem characteristics:
- *Color.*—About Light Yellow-Green145D to Light Yellow-Green 145C.
- *Position of hairs.*—Slightly outwards.
- *Length.*—Medium, about 12 cm.

Terminal leaflet:
- *Length/width ratio.*—As long as broad.
- *Length.*—Medium (About 6.5 to 7 cm).
- *Width.*—Medium (About 6.5 to 7 cm).
- *Shape of base.*—Acute.
- *Margin.*—Crenate.
- *Shape in cross section.*—Convex.
- *Shape of apex.*—Obtuse.
- *Margin.*—Crenate.

Petiole:
- *Position of hairs.*—Slightly outwards.
- *Length.*—Medium, about 12 cm.
- *Typical and observed petiole diameter.*—About 3 mm to 4 mm.

Stipule:
- *Anthocyanin coloration.*—Weak, about Light Greyed-Red 179D to Medium Greyed-Red 179C.

Stolons:
- *Number.*—About 8.
- *Anthocyanin coloration.*—Absent or weak, about Light Yellow-Green 145D to Light Yellow-Green 145C.
- *Thickness.*—Medium, about 0.3 to 0.34 cm.
- *Pubescence.*—Medium.
- *Length.*—Medium (about 34 to 38 cm).
- *Color.*—About Light Yellow-Green 145D to Light Yellow-Green 145C.

Inflorescence:
- *Position relative to foliage.*—Level with.
- *Number of flowers.*—Medium to many, about 7 to 10.

Pedicel:

*Attitude of hairs.*—Slightly outwards.

Flower:

*Color.*—About White 155D to White 155C.

*Diameter.*—Large, about 2.8-3.2 cm.

*Size of calyx relative to corolla.*—Larger.

*Arrangement of petals.*—Overlapping.

*Diameter primary flowers.*—Long, about 2.8-3.2 cm.

*Diameter secondary flowers.*—Medium, about 2.4-2.8 cm.

*Number of petals.*—About 5-7.

*Fragrance.*—No significant fragrance.

*Time from bloom to mature fruit* (*Huelva, Spain*).—About 32 to 37 days.

*Stamens.*—Present, about 3.6 to 3.2 cm.

*Stamens color.*—About White 155D to White 155C.

*Anthers size.*—Medium.

*Anthers color.*—About Medium Yellow 12C to Medium Yellow 13C.

*Pollen.*—Abundant.

*Pollen color.*—About Medium Yellow-Orange 16C to Medium Yellow-Orange 17D.

*Pistils.*—Abundant.

*Pistils size.*—Medium.

*Pistils color.*—About Medium Yellow group 13C to Medium Yellow 14C.

Petal:

*Length/width ratio.*—Moderately shorter.

*Length.*—Long (Approximately 1.0 to 1.2 cm).

*Width.*—Long (Approximately 1.4 to 1.7 mm).

*Shape.*—Slightly ovate.

*Color.*—About White 155D to White 155C.

*Shape of apex.*—Rounded.

*Margin.*—Glabro.

*Shape of base.*—Obtuse.

Fruit:

*Ratio of length/maximum width.*—Moderately longer.

*Color.*—About Dark Orange-Red 33A to Dark Orange-Red 34A.

*Eveness of color.*—Even or very slightly uneven.

*Size.*—Medium.

*Shape.*—Conical.

*Glossiness.*—Weak.

*Length.*—Long (About 5.5 to 6.0 cm).

*Width.*—Medium (About 4.0 to 4.5 cm).

*Difference in shapes of terminal other fruits.*—Moderate.

*Width of band without achenes.*—Absent of very narrow.

*Color of achenes.*—About Medium Orange-Red 29A to Medium Orange-Red 30D.

*Position of achenes.*—Below surface.

*Evenness of surface.*—Slightly uneven.

*Position of calyx.*—Raised.

*Attitude of sepals.*—Upwards.

*Pose of the calyx segments.*—Spreading.

*Diameter of calyx in relation to diameter of fruit.*—Slightly smaller.

*Calyx.*—Number of sepals about 7-8 and 4-6, in addition, smaller shape of sepals: lanceolate and pointed the smaller ones.

*Adherence of calyx.*—Strong.

*Color upperside of sepals.*—About Medium Green 138B to Medium Green 139B.

*Color underside of sepals.*—About Light Yellow-Green 147D to Light Yellow-Green 148D.

*Length of sepals.*—Long (About 15 to 20 mm).

*Width of sepals.*—Long (About 8 to 10 mm).

*Firmness.*—Medium.

*Color of flesh.*—About Medium Orange-Red 31C to Dark Orange-Red 33B.

*Color of core.*—About Light Orange-Red 31D to Medium Orange-Red 31C.

*Cavity.*—Absent or small.

*Distribution of red color of flesh.*—Only marginal.

*Hollow center.*—Weakly expressed.

*Sweetness.*—Medium. 8.3° Brix.

*Acidity.*—Medium. 0.50%.

*Time of flowering* (50% *of plants at first flower*).—Early.

*Time of ripening* (50% *of plants with ripe fruits*).—Early.

*Type of bearing.*—Not remontant.

*Chilling.*—Weak, about 100 to 200 hours.

Disease resistance: No particular sensitivity to any disease or parasite has been observed for 'Safari'.

Storage qualities: 'Safari' fruit maintain their quality characteristics when keeping them in a frigo chamber at temperatures of about 2° C. during 48 hours. The fruit's color remains substantially the same.

I claim:

1. A new and distinct strawberry plant of the variety substantially as illustrated and described.

* * * * *

06.44H.216

06.44H.216